United States Patent
Chung et al.

(10) Patent No.: US 8,263,095 B2
(45) Date of Patent: Sep. 11, 2012

(54) METHODS OF USE FOR PEPTIDES HAVING ACTIVITIES OF INSULIN LIKE GROWTH FACTOR-1

(75) Inventors: Yong Ji Chung, Gyeonggi-do (KR); Young Deug Kim, Gyeonggi-do (KR); Eun Mi Kim, Jeollanam-do (KR)

(73) Assignee: Caregen Co., Ltd., Gyeonggi-do (KR)

( * ) Notice: Subject to any disclaimer, the term of this patent is extended or adjusted under 35 U.S.C. 154(b) by 0 days.

(21) Appl. No.: 12/659,546

(22) Filed: Mar. 12, 2010

(65) Prior Publication Data

US 2010/0278756 A1 Nov. 4, 2010

Related U.S. Application Data

(62) Division of application No. 12/224,788, filed as application No. PCT/KR2007/001086 on Mar. 6, 2007, now abandoned.

(30) Foreign Application Priority Data

Mar. 6, 2006 (KR) ........................ 10-2006-0021099

(51) Int. Cl.
*A61K 8/64* (2006.01)
*A61K 8/00* (2006.01)
*A61K 38/30* (2006.01)
*A61K 38/08* (2006.01)
*C07K 14/65* (2006.01)

(52) U.S. Cl. .......... 424/401; 530/328; 530/300; 514/8.6
(58) Field of Classification Search ........................ None
See application file for complete search history.

(56) References Cited

U.S. PATENT DOCUMENTS

| | | | | |
|---|---|---|---|---|
| 5,652,214 A | * | 7/1997 | Lewis et al. | 514/12 |
| 6,034,062 A | * | 3/2000 | Thies et al. | 514/12 |
| 2002/0081324 A1 | * | 6/2002 | Twine | 424/401 |

FOREIGN PATENT DOCUMENTS

KR 10-2004-0076780 * 9/2004

* cited by examiner

*Primary Examiner* — Elly-Gerald Stoica
(74) *Attorney, Agent, or Firm* — Nath, Goldberg & Meyer; Tanya E. Harkins

(57) ABSTRACT

The present invention relates to a peptide having the activity of insulin like growth factor-1 (IGF-1) and derived from IGF-1, a composition for improving skin conditions or treating a periodontal disease comprising the peptide. The IGF-1 mimicking peptides of this invention have identical functions or actions to natural-occurring IGF-1 and much better stability and skin permeation than natural-occurring IGF-1. In these connections, the composition comprising the peptides of this invention can exhibit excellent efficacies on the treatment, prevention and improvement of diseases or conditions demanding IGF-1 activities. In addition, the peptides of this invention can be advantageously applied to pharmaceutical compositions, quasi-drugs and cosmetics.

5 Claims, 16 Drawing Sheets

Fig. 1

```
1                                      10                                       20
Gly Pro Glu Thr Leu Cys Gly Ala Glu Leu Val Asp Ala Leu Gln Phe Val Cys Gly Asp 21                                     30                                       40
Arg Gly Phe Tyr Phe Asn Lys Pro Thr Gly Tyr Gly Ser Ser Ser Arg Arg Ala Pro Gln
                            ═══════════════Sequence 1═══════════════════════════
                                          ·········································
                                                          Sequence 2

41                                     50                                       60
Thr Gly Ile Val Asp Glu Cys Cys Phe Arg Ser Cys Asp Leu Arg Arg Leu Glu Met Tyr
·······                    ─ ─ ─ ─ ─ ─ ─ ─ ─ ─ ─ ─ ─ ─ ─ ─ ─ ─
                                          Sequence 3
                                                    ─ · ─ · ─ · ─ · ─ · ─ · ─ · ─
                                                          Sequence 4

61                       70                                        Sequence 5
Cys Ala Pro Leu Lys Pro Ala Lys Ser Ala
─ · ─
───────────────────────
```

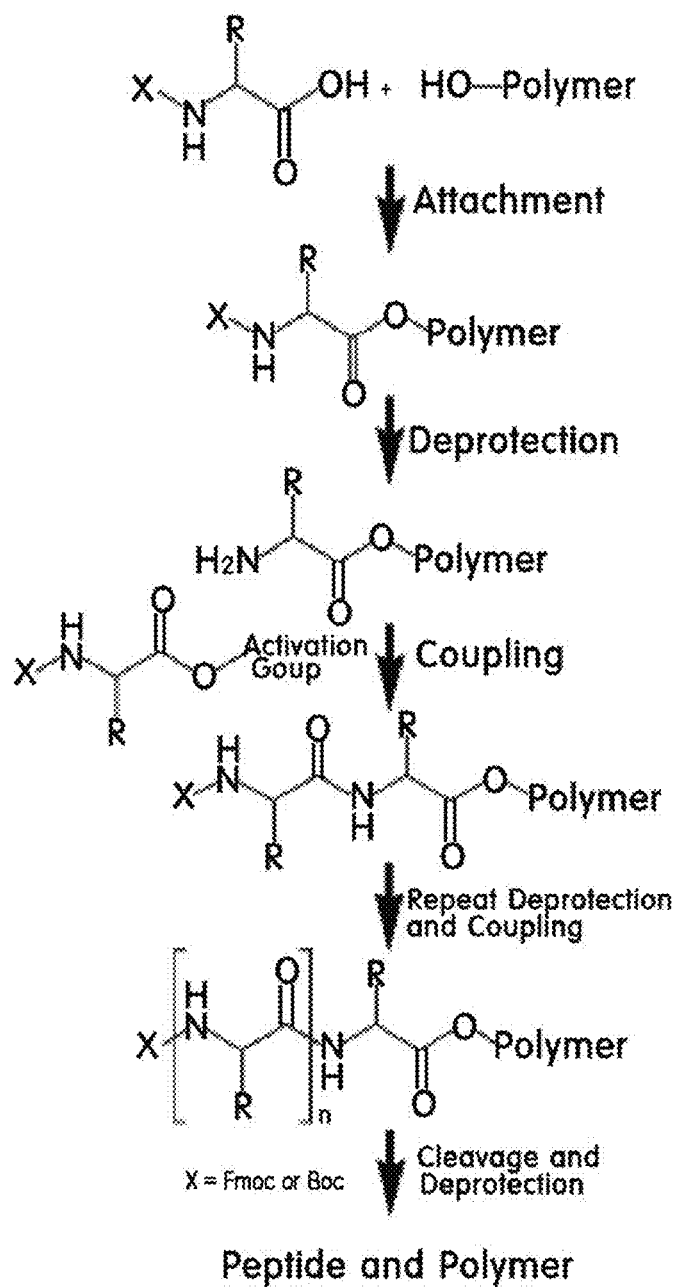

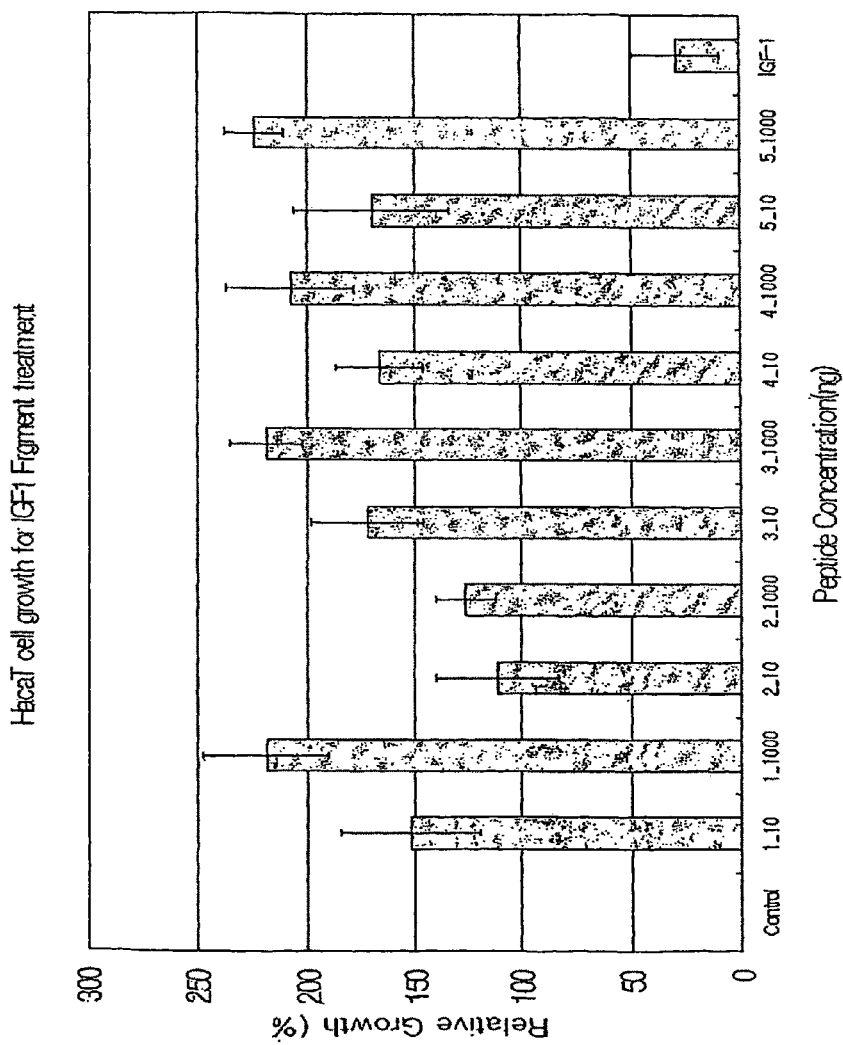

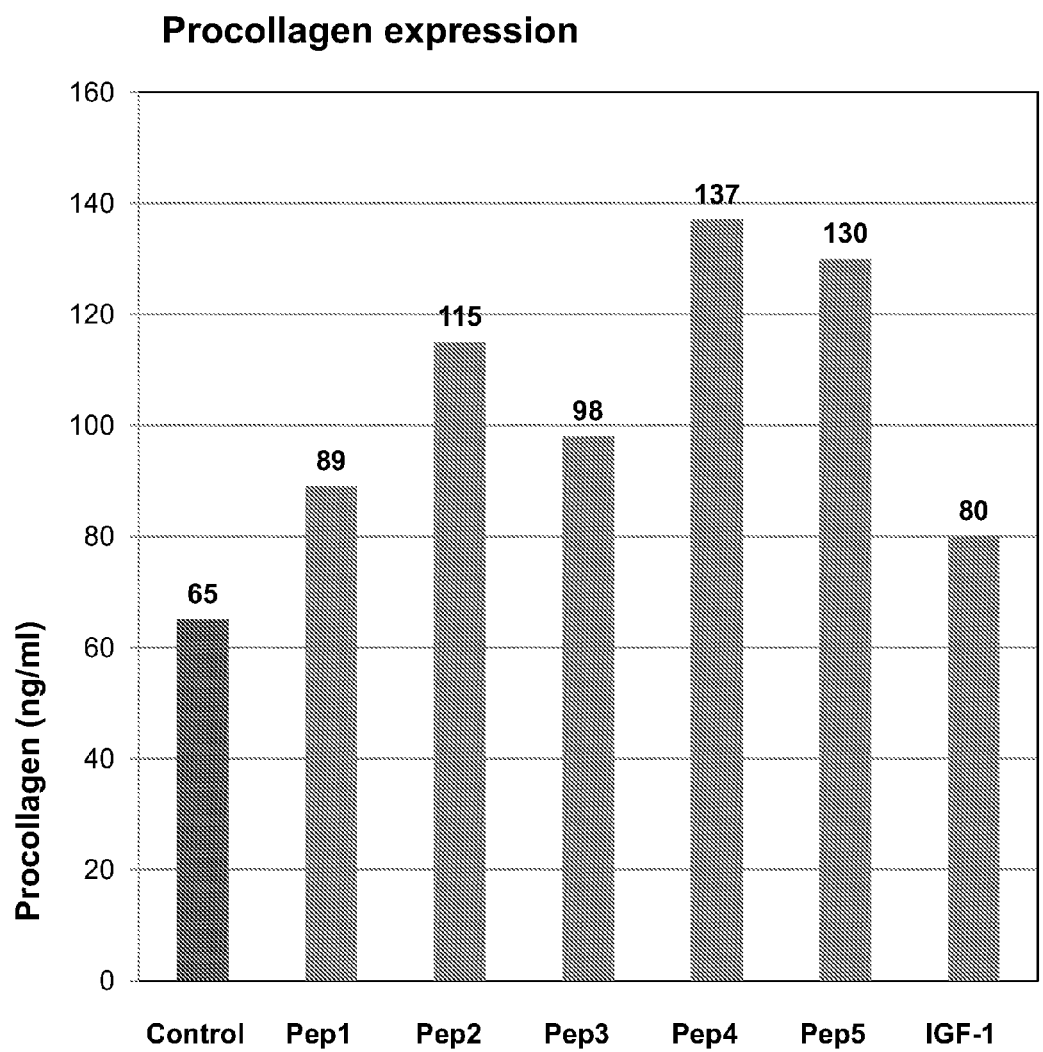

SEQUENCE LISTING

```
<160> NUMBER OF SEQ ID NOS: 8

<210> SEQ ID NO 1
<211> LENGTH: 16
<212> TYPE: PRT
<213> ORGANISM: Artificial Sequence
<220> FEATURE:
<223> OTHER INFORMATION: IGF-1 mimicking peptide 1

<400> SEQUENCE: 1

Gly Phe Tyr Phe Asn Lys Ala Ala Gly Tyr Gly Ser Ser Ser Arg Arg
```

```
                             1               5                  10                  15

<210> SEQ ID NO 2
<211> LENGTH: 12
<212> TYPE: PRT
<213> ORGANISM: Artificial Sequence
<220> FEATURE:
<223> OTHER INFORMATION: IGF-1 mimicking peptide 2

<400> SEQUENCE: 2

Gly Tyr Gly Ser Ser Ser Arg Arg Ala Pro Gln Thr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: IGF-1 mimicking peptide 3

<400> SEQUENCE: 3

Glu Ser Ser Phe Arg Ser Ser Asp Leu Arg Arg Leu
1               5                   10

<210> SEQ ID NO 4
<211> LENGTH: 10
<212> TYPE: PRT
<213> ORGANISM: Artificial Sequence
<220> FEATURE:
<223> OTHER INFORMATION: IGF-1 mimicking peptide 4

<400> SEQUENCE: 4

Cys Asp Leu Arg Arg Leu Glu Met Tyr Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: IGF-1 mimicking peptide 5

<400> SEQUENCE: 5

Arg Arg Leu Glu Met Tyr Cys Ala Pro Leu Lys Pro
1               5                   10

<210> SEQ ID NO 6
<211> LENGTH: 24
<212> TYPE: PRT
<213> ORGANISM: Artificial Sequence
<220> FEATURE:
<223> OTHER INFORMATION: IGF-1 mimicking peptide 6
<220> FEATURE:
<221> NAME/KEY: DOMAIN
<222> LOCATION: (7)..(17)
<223> OTHER INFORMATION: Xaa can be any amino acid or peptide linker
      and can vary from between 1 to 10 amino acids.

<400> SEQUENCE: 6

Gly Phe Tyr Phe Asn Lys Xaa Xaa Xaa Xaa Xaa Xaa Xaa Xaa Xaa
1               5                   10                  15

Gly Tyr Gly Ser Ser Ser Arg Arg
                20

<210> SEQ ID NO 7
<211> LENGTH: 16
<212> TYPE: PRT
<213> ORGANISM: Artificial Sequence
```

```
-continued

<220> FEATURE:
<223> OTHER INFORMATION: IGF-1 mimicking peptide 7

<400> SEQUENCE: 7

Gly Phe Tyr Phe Asn Lys Pro Thr Gly Tyr Gly Ser Ser Ser Arg Arg
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: IGF-1 mimicking peptide 8

<400> SEQUENCE: 8

Glu Cys Cys Phe Arg Ser Cys Asp Leu Arg Arg Leu
1               5                   10
```

METHODS OF USE FOR PEPTIDES HAVING ACTIVITIES OF INSULIN LIKE GROWTH FACTOR-1

This is a Divisional Application of U.S. patent application No. 12/224,788, filed Sep. 5, 2008, which was filed under 35 U.S.C. 371 as a national stage of International Application No. PCT/KR2007/001086, filed Mar. 6, 2007, an application claiming foreign priority benefits under 35 U.S.C. 119 of Korean Application No. 10-2006-0021099, filed Mar. 6, 2006, the content of each of which is hereby incorporated by reference in its entirety.

BACKGROUND OF THE INVENTION

1. Field of the Invention

The present invention relates to peptides having insulin like growth factor-1 (IGF-1) and theirs uses.

2. Description of the Related Art

Insulin like growth factor-1 (IGF-1) with a molecular weight of 7,649 Da consisting of 70 amino acids is generated by human growth hormone in the liver and then secreted in blood. Its amino acid composition shows about 43% similarity to A chain of insulin. IGF-1 exhibiting similar actions to insulin is capable of binding to insulin receptor as well as its receptor, and promoting cell proliferation. IGF-1 is usually called somatomedin C due to its growth mediation activity.

It has been reported that the IGF-1 receptor is present in various tissues such as adipose tissue, lymphocyte, bond and placental membrane as well as hepatocyte. IGF-1 receptor has been revealed to have other signaling pathway than insulin receptor. The binding of IGF-1 to its receptor results in promoting somatic cell division through second messengers. IGF-1 secreted into blood from the liver is circulated as the complex form with binding protein (inactivated form). IGF-1 is separated from its binding protein in response to physiological changes or some nutrient conditions and then binds to receptors on somatic cell to stimulate cells.

IGF-1 serves to promote growth of almost all types of cells in vivo and to inhibit synthesis of glucagon in carbohydrate metabolism, resulting in the enhancement of glucose absorption into cells. Due to its similar actions to insulin, it has been focused as promising therapeutics for Laron dwarfism and insulin dependent or independent diabetes. In addition, IGF-1 having immunmodulatory activity has been researched to provide therapeutics to increase immune response of post-surgery patients and to modulate hypersensitivity reactions induced by sepsis. In particular, IGF-1 facilitates synthesis of proteoglycan in chondrocytes and serves as promising therapeutics for degenerative arthritis caused by degradation of proteoglycan in cartilage to destruct cartilage. Therefore, IGF-1 has been highlighted as a biomolecule applicable to immunmodulation and the treatment of diabetes, dwarfism, degenerative arthritis and amyotrophic lateral sclerosis.

IGF-1 has three disulfide bonds (amino acid 6-48, 18-61 and 47-52) in its backbone which is essential to its inherent activities, comprising B (1-29), C (30-41), A (42-62) and D (63-70) domains. Of them, B and A domains have been reported as a binding domain to its receptor and C and D domains have been suggested to assist a specific binding of B and A domains to IGF-1 receptor. The deletion or mutation of C and D domains permits the binding affinity of IGF-1 to be altered in which IGF-1 variants bind preferentially to insulin receptor rather than IGF-1 receptor.

For mass production of IGF-1, many researchers have made intensive researches on production of the recombinant protein using *E. coli* expression systems. However, these preparations are encountered to need of time- and cost-consuming refolding process and of complex purification process to remove *E. coli*-originated contaminants. To be free from such shortcomings, IGF-1 mimicking peptides have been prepared by solid phase synthesis methods. For instance, U.S. Pat. No. 5,473,054 filed by Jameson et al. discloses that JB2 (corresponding to amino acid 29-38 of IGF-1) and JB1 (corresponding to amino acid 61-70) fragment have cell proliferation potential and the enantiomer of JB1, JB3 has inhibitory activity to IGF-1. WO 03/048192 filed by Teruo et al. teaches that each of the peptide fragment of IGF-1 consisting of amino acid 33-37 and substance-P derived tetrapeptide exert complementary efficacy to wound healing. In addition, Kodama et al. reports that the peptide fragment of IGF-1 consisting of amino acid 50-70 has a therapeutic effect to diabetes in mice (*Autoimmunity*, 37:481-487 (2004)).

Throughout this application, various patents and publications are referenced, and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

For developing peptides having actions identical to natural-occurring IGF-1 and having more significant characteristics such as activity, skin penetration and stability than natural-occurring IGF-1, the present inventors have made intensive researches. As a result, the present inventors have discovered several IGF-1 mimicking peptides having excellent characteristics described above on the basis of the amino acid sequence of natural-occurring IGF-1, eventually accomplishing the present invention.

Accordingly, it is one object of this invention to provide a peptide having the activity of IGF-1.

It is another object of this invention to provide a composition for improving skin conditions or treating a periodontal disease.

It is still another object of this invention to provide a method for improving a skin condition or treating a periodontal disease.

It is further object of this invention to provide a use of the peptide of the present invention for manufacturing a composition for improving a skin condition or treating a periodontal disease.

Other objects and advantages of the present invention will become apparent from the following detailed description together with the appended claims and drawings.

In one aspect of this invention, there is provided a peptide having the activity of insulin like growth factor-1 (IGF-1) and derived from IGF-1, which comprises the amino acid sequence selected from SEQ ID NOs:2-8.

In another aspect of this invention, there is provided a composition for improving skin conditions or treating a periodontal disease, which comprises as an active ingredient the peptide of this invention.

In still another aspect of this invention, there is provided a method for improving a skin condition or treating a periodontal disease, which comprises administering to a subject a composition comprising the peptide of this invention.

In further aspect of this invention, there is provided a use of the peptide of the present invention for manufacturing a composition for improving a skin condition or treating a periodontal disease.

For developing peptides having actions identical to natural-occurring IGF-1 and having more significant characteristics such as activity, skin penetration and stability than natural-occurring IGF-1, the present inventors have made intensive researches. As a result, the present inventors have discovered several IGF-1 mimicking peptides having excellent characteristics described above on the basis of the amino acid sequence of natural-occurring IGF-1.

The peptide of the present invention comprises the IGF-1-derived amino acid sequence selected from SEQ ID NOs:2-8. Preferably, the peptide consists essentially of the amino acid sequence selected from SEQ ID NOs:2-8. Most Preferably, the peptide consists of the amino acid sequence selected from SEQ ID NOs:2-8.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.* 85:2149-54 (1963); Stewart, et al., *Solid Phase Peptide Synthesis,* 2nd. ed., Pierce Chem. Co.: Rockford, 111 (1984)).

The design of peptides according to the present invention is exemplified in FIG. 1.

SEQ ID NO:7 corresponds to amino acids 22-37 of natural-occurring IGF-1. In SEQ ID NO:7, it is preferable that amino acids 28-29 are substituted by other amino acid residues for stronger binding to its receptor, which generates a novel sequence, SEQ ID NO:6.

One embodiment of the amino acid sequence of SEQ ID NO:6 is represented by "Gly-Phe-Tyr-Phe-Asn-Lys-Xaa-Gly-Tyr-Gly-Ser-Ser-Ser-Arg-Arg" due to limitations of a computer program producing a sequence listing in patent specification. Therefore, more exactly, SEQ ID NO:6 is represented by "Gly-Phe-Tyr-Phe-Asn-Lys-(Xaa)$_n$-Gly-Tyr-Gly-Ser-Ser-Ser-Arg-Arg", wherein Xaa is a linker (peptide linker), n is an integer of 1-10 (preferably, 1-8, more preferably 1-5, most preferably 2).

The linker contained in SEQ ID NO:6 comprises any linker available to one of skill in the art. Preferably, the linker comprises a plurality of amino acids. Details of peptide linkers are found in Huston, et al., *Methods in Enzymology,* 203:46-88 (1991), and Whitlow, et al., *Protein Eng.,* 6:989 (1993), teachings of which are incorporated herein by references. A suitable linker in the present invention comprises amino acids having uncharged side chains, preferably, Gly, Ser, Ala and Cys, most preferably Ala. According to the most preferable embodiment, the linker contained in SEQ ID NO:6 is Ala-Ala dimer, hexanoic acid or amino butyric acid.

According to the most preferable embodiment, the specific amino acid sequence of SEQ ID NO:6 is set forth in SEQ ID NO:1.

SEQ ID NO:2 corresponds to amino acids 30-41 of IGF-1.
SEQ ID NO:8 corresponds to amino acids 46-57 of IGF-1. For elevating activities of the peptide of SEQ ID NO:8, a Cys residue is preferably substituted with a Ser residue, which generates a novel sequence, SEQ ID NO:3.

SEQ ID NO:4 corresponds to amino acids 52-61 of IGF-1. Preferably, in the amino acid sequence of SEQ ID NO:4, Cys residues at the N- and C-terminal are linked to form a disulfide bond, producing a cyclized peptide for enhancing the stability of peptides.

Even though the peptides of this invention per se have higher stability than natural-occurring IGF-1, their modification enables to have much higher stability. Preferably, the C-terminal of the peptides of the present invention is modified to have a hydroxyl group (—OH) or an amino group (—NH$_2$).

According to a preferred embodiment, the N-terminal of the peptides of the present invention is protected with a protection group selected from the group consisting of acetyl group, fluorenyl methoxy carbonyl group, formyl group, palmitoyl group, myristyl group, stearyl group or polyethylene glycol (PEG).

The modifications of peptides described above greatly increase the stability of peptides of this invention. The term used herein "stability" refers to in vivo stability and storage stability (e.g., storage stability at room temperature) as well. The protection group described above protects the peptides from the attack of protease in vivo.

The composition of the present invention is utilized to prevent or treat IGF-1-effective (insulin like growth factor-1-effective) disorders or conditions.

The peptide of this invention as active ingredients contained in the present composition has IGF-1 activities and shows in vivo functions and efficacies identical or similar to natural-occurring IGF-4. The term used herein "IGF-1 activities" refers to any and all activities of natural-occurring IGF-1 known to one of skill in the art, for example, including promotion of cell proliferation division. Since the peptide of this invention is prepared to mimic the actions of natural-occurring IGF-1, it can exert all in vivo activities of natural-occurring IGF-1.

Because the peptide of this invention exhibits functions and actions identical or similar to natural-occurring IGF-1 and shows higher biological activities than natural-occurring IGF-1, it can be advantageously applied for preventing or treating IGF-1-effective disorders or conditions. The term used herein "IGF-1-effective disorders or conditions" refers to disorders or conditions able to be prevented or treated by natural-occurring IGF-1.

According to a preferred embodiment, the actions of the preset composition may be expressed as improvement of skin conditions or treatment of periodontal diseases.

Where the present composition is applied to periodontal diseases, it may be formulated into toothpaste or a composition for tooth and mouth cleaning or caring. The term "composition for treating periodontal diseases" may be interchangeably used herein with other terms, "composition for tooth and mouth caring" and "composition for tooth and mouth cleaning". The peptide of this invention promotes biological activities of epidermal cells present in gum tissues and heals gum wound to regenerate damaged gum tissues, thereby treating or preventing periodontal diseases.

According to a more preferred embodiment, the present composition has efficacies or activities to improve skin conditions. In particular, the peptides used as active ingredients in the present composition show excellent skin permeation because of their low molecular weight. Accordingly, where the present composition is topically applied to skin, it becomes evident that skin conditions are considerably improved. More still preferably, the improvement in the skin condition by the present composition includes the improvement in wrinkle or skin elasticity, the prevention of skin aging, the prevention of hair loss, the promotion of hair growth, the improvement in skin moisture, the removal of dark spots, the treatment of acne, wound healing and skin regeneration, most preferably, the improvement in wrinkle or skin elasticity, and the prevention of skin aging, wound healing and skin regeneration.

For example, the peptides used as active ingredients in the present composition promote the proliferation of keratinocytes, induce the biosynthesis of procollagen, laminin and fibronectin to regenerate keratinocyte layer, epidermis and dermis, thereby resulting in the improvements in wrinkle, skin elasticity and skin moisture, the prevention of skin aging, wound healing, skin regeneration and gum tissue regeneration.

The present composition may be prepared as a pharmaceutical or cosmetic composition.

According to a preferred embodiment, the composition is a pharmaceutical composition comprising (a) a pharmaceutically effective amount of the peptides of the present invention; and (b) a pharmaceutically acceptable carrier.

The term used herein "pharmaceutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, intraperitoneal, intramuscular, subcutaneous, transdermal or local administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 μg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferred embodiment, the composition is a cosmetic composition comprising (a) a cosmetically effective amount of the peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

The features and advantages of the present invention will be summarized as follows:

(i) the IGF-1-mimicking peptides of the present invention posses identical functions or activities to natural-occurring IGF-1;

(ii) the peptides of the present invention is much higher stability and skin penetration potency than natural-occurring IGF-1;

(iii) therefore, the composition comprising the peptide exhibits excellent treatment and prevention efficacies on diseases or conditions demanding IGF-1 activities; and (iv) the peptide of this invention can be advantageously applied to pharmaceutical compositions, quasi-drugs and cosmetics.

BRIEF DESCRIPTION OF THE DRAWINGS

FIG. 1 represents the amino acid sequence of natural-occurring insulin like growth factor-1 (IGF-1) and selected regions for preparing peptides of the present invention.

FIG. 2 schematically represents processes for preparing peptides of the present invention.

FIG. 8 shows influence of peptides of this invention on growth of keratinocytes. The numbers indicated in x-axis are types and amounts of peptides. For example, "1_10" and "1_1000" represent the results of treatments with 10 ng and 1000 ng of the peptide of SEQ ID NO:1, respectively.

FIG. 10 represents analysis results on elevated procollagen level in cell culture incubated with peptides of this invention. Pep 1-5 denote peptides of SEQ ID NOs:1-5, respectively.

Figure 3:
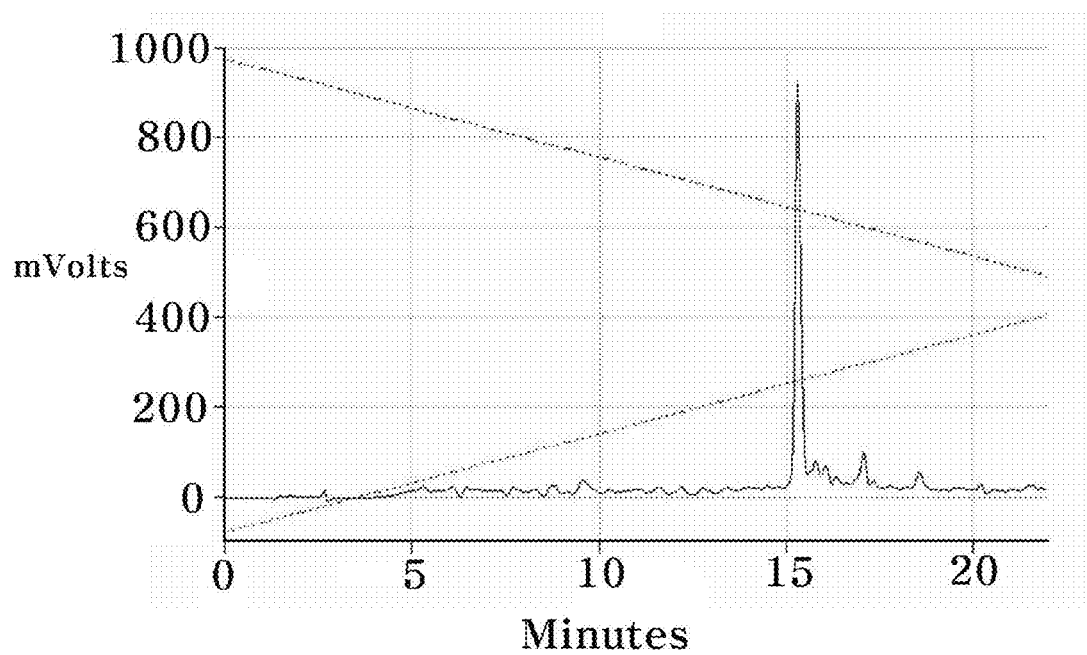
FIG. 3 represents results of high performance liquid chromatography analysis of the peptide of SEQ ID NO:1 prepared in Example.
Figure 4:
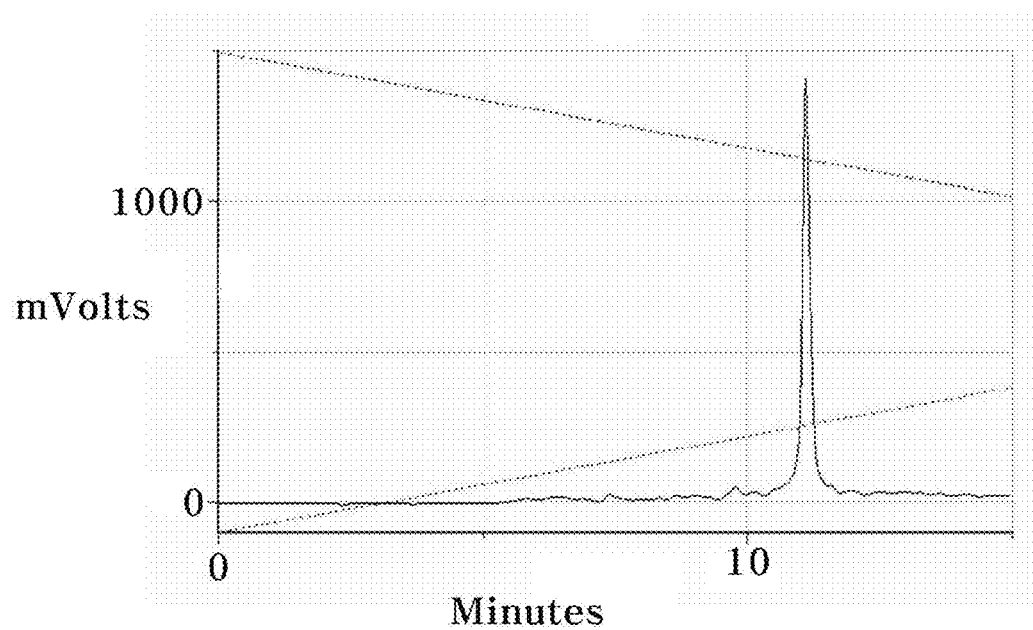
FIG. 4 represents results of high performance liquid chromatography analysis of the peptide of SEQ ID NO:2 prepared in Example.
Figure 5:
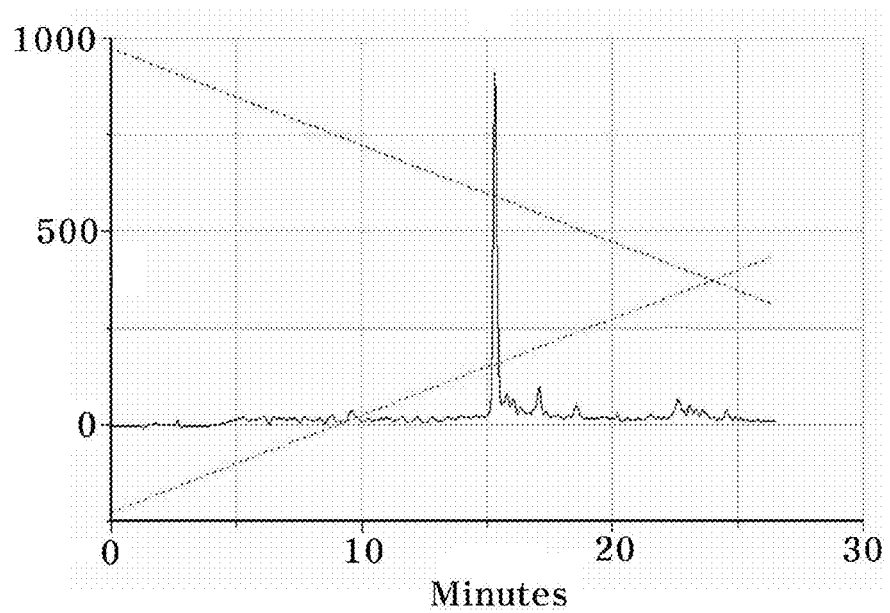
FIG. 5 represents results of high performance liquid chromatography analysis of the peptide of SEQ ID NO:3 prepared in Example.
Figure 6:
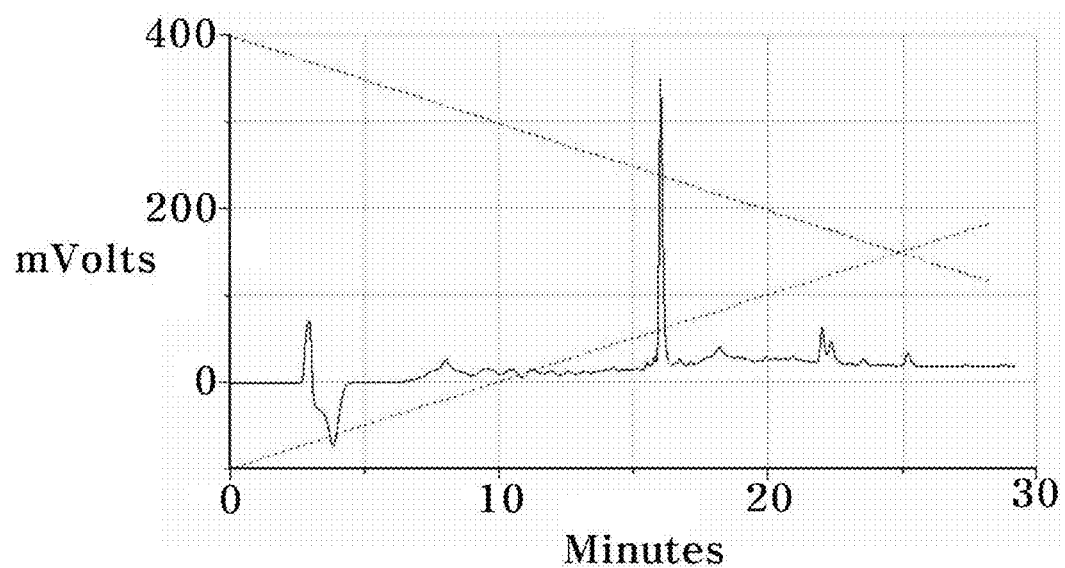
FIG. 6 represents results of high performance liquid chromatography analysis of the peptide of SEQ ID NO:4 prepared in Example.
Figure 7:
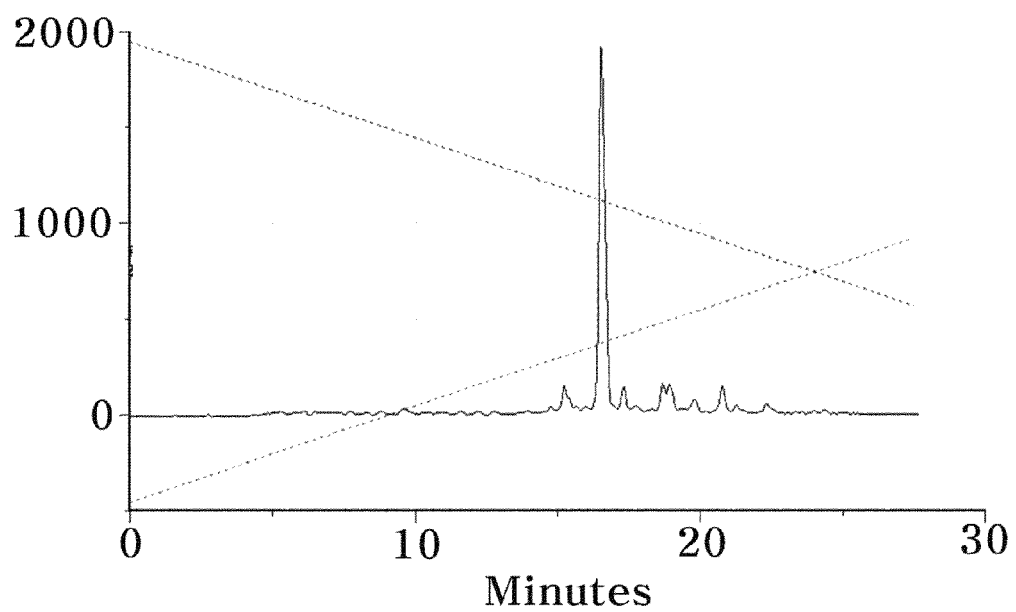
FIG. 7 represents results of high performance liquid chromatography analysis of the peptide of SEQ ID NO:5 prepared in Example.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation Example 1

Synthesis of Gly-Phe-Tyr-Phe-Asn-Lys-Ala-Ala-Gly-Tyr-Gly-Ser-Ser-Ser-Arg-Arg (SEQ ID NO:1)

To 700 mg of chloro trityl chloride resin (CTL resin, Nova Biochem Cat No. 01-64-0021) introduced into a reactor were added 10 ml of methylene chloride (MC) and agitated for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Arg(pbf)-OH and 400 mmole of diisopropyl ethylamine (DIEA) were then added to the reactor, after which the mixture was dissolved by agitation and reaction was then undertaken with agitating for 1 hr. After reaction, the resultant was washed and reacted for 10 min in methanol and DIEA (2:1) dissolved in DCM, followed by washing with excess DCM/DMF (1:1). Following the removal of the solvent, 10 ml of DMF were added to the reactor and agitated for 3 min. followed by removing the solvent. 10 ml of a deprotection solution (20% piperidine/DMF) were added to the reactor and agitated for 10 min at room temperature and solution removal was performed. After adding the same volume of the deprotection solution, the reaction was undertaken for 10 min and solution was removed, followed by washing sequentially with DMF, MC and DMF to yield Arg-(pbf)-CTL resins. 10 ml of DMF solution was added to a new reactor and then 200 mmole of Fmoc-Arg(pbf)-OH, 200 mmole of HoBt and 200 mmole of Bop were added, followed by agitation for solubilization. 400 mmole of DIEA was added to the reactor and agitation was carried out to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution to remove unreacted residuals. A small amount of the reacted resin was taken to evaluate extent of reactions by Ninhydrine test. Using the deprotection solution, the deprotection was performed twice in the same manner as described above to yield Arg-(pbf)-Arg-(pbf)-CTL resins. After washing with DMF and MC, Ninhydrine test was carried out and then the attachments of amino acids were performed as described above. Based on the amino acid sequence depicted in FIG. 1, Fmoc-Ser(tBu), Fmoc-Ser(tBu), Fmoc-Ser(tBu), Fmoc-Gly, Fmoc-Tyr(tBu), Fmoc-Gly, Fmoc-Ala, Fmoc-Ala, Fmoc-Lys(Boc), Fmoc-Asn(trt), Fmoc-Phe, Fmoc-Tyr(tBu), Fmoc-Phe and Fmoc-Gly were sequentially attached to resins. Fmoc-protecting group was removed by incubating with the deprotection solution twice for 10 min. The prepared peptidyl resins were washed three times sequentially with DMF, MC and methanol, dried under the flow of nitrogen gas, completely dried by vacuum-drying under $P_2O_5$ and then reacted with 30 ml of the leaving solution [containing 81.5%. TFA, 5% distilled water, 5% thioanisole, 5% phenol, 2.5% EDT and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.18 g of unpurified GFYFN-KAAGYGSSSRR (yield 69.6%). The molecular weight of the final product was determined as 1770.6 (theoretical MW 1769.9) using a mass analyzer.

Preparation Example 2

Synthesis of Other Peptides

The peptides of SEQ ID NOs:2-5 were synthesized as processes described in Preparation Example 1. SEQ ID NO:2 (Gly-Tyr-Gly-Ser-Ser-Ser-Arg-Arg-Ala-Pro-Gln-Thr: GYGSSSRRAPQT) corresponds to amino acids 30-41 of IGF-1, SEQ ID NO:3 (Glu-Ser-Ser-Phe-Arg-Ser-Ser-Asp-Leu-Arg-Arg-Leu: ESSFRSSDLRRL) to amino acids 46-57 of IGF-1, SEQ ID NO:4 (Cys-Asp-Leu-Arg-Arg-Leu-Glu-Met-Tyr-Cys: CDLRRLEMYC) to amino acids 52-61 of IGF-1, and SEQ ID NO:5 (Arg-Arg-Leu-Glu-Met-Tyr-Cys-Ala-Pro-Leu-Lys-Pro: RRLEMYCAPLKP) to amino acids 55-66 of IGF-1.

The determined molecular weights of the peptides are summarized in Table 1.

TABLE 1

| SEQ ID NO | Amino acid sequence | Analyzed values (mass analyzer) | |
|---|---|---|---|
| | | Analyzed values | Theoretical values |
| 1 | GFYFNKAAGYGSSSRR | 1770.6 | 1767.9 |
| 2 | GYGSSSRRAPQT | 1270.88 | 1266.4 |
| 3 | ESSFRSSDLRRL | 1457.4 | 1452.6 |
| 4 | CDLRRLEMYC | 1304.8 | 1303.6 |
| 5 | RRLEMYCAPLKP | 1479.5 | 1476.8 |

Preparation Example 3

Synthesis of Cys-Asp-Leu-Arg-Arg-Leu-Glu-Met-Tyr-Cys (1,10 Cyclized CDLRRLEMYC)

To increase the stability of the peptide of SEQ ID NO:4 prepared in Preparation Example 2, the cyclization was carried out using Cys residues at the C- and N-terminal. 100 mg of the peptide of SEQ ID NO:4 (Cys-Asp-Leu-Arg-Arg-Leu-Glu-Met-Tyr-Cys-OH) were dissolved in 1 L of 10% DMSO/deprotection distilled water. After fixing pH to 8.0, the peptide solution was agitated for 8 hr under air to induce oxidation. By preparative chromatography, 40 mg of cyclized Cys-Asp-Leu-Arg-Arg-Leu-Glu-Met-Tyr-Cys-OH (1,10 cyclized). The molecular weight of the final cyclized peptide was determined as 1302.8 using a mass analyzer.

Preparation Example 4

Synthesis of FITC-b-Ala-Cys-Asp-Leu-Arg-Arg-Leu-Glu-Met-Tyr-Cys (2,11 Cyclized FITC-b-Ala-CDLRRLEMYC)

To 700 mg of chloro trityl chloride resin (CTL resin, Nova Biochem Cat No. 01-64-0021) introduced into a reactor were added 10 ml of methylene chloride (MC) and agitated for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Cys(trt)-OH and 400 mmole of diisopropyl ethylamine (DIEA) were then added to the reactor, after which the mixture was dissolved by agitation and reaction was then undertaken with agitating for 1 hr. After reaction, the resultant was washed and reacted for 10 min in methanol and DIEA (2:1) dissolved in DCM, followed by washing with excess DCM/DMF (1:1). Following the removal of the solvent, 10 ml of DMF were added to the reactor and agitated for 3 min. followed by removing the solvent. 10 ml of a deprotection solution (20% piperidine/DMF) were added to the reactor and agitated for 10 min at room temperature and solution removal was performed. After adding the same volume of the deprotection solution, the reaction was undertaken for 10 min and solution was removed, followed by washing sequentially with DMF, MC and DMF to yield Cys-(trt)-CTL resins. 10 ml of DMF solution was added to a new reactor and then 200 mmole of Fmoc-Tyr(tBu)-OH, 200 mmole of HoBt and 200 mmole of Bop were added, followed by agitation for solubilization. 400 mmole of DIEA was added to the reactor and agitation was carried out to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution to remove unreacted residuals. A small amount of the reacted resin was taken to evaluate extent of reactions by Ninhydrine test. Using the deprotection solution, the deprotection was performed twice in the same manner as described above to yield Tyr-(tBu)-Cys-(trt)-CTL resins. After washing with DMF and MC, Ninhydrine test was carried out and then the attachments of amino acids were performed as described above. Based on the amino acid sequence depicted in FIG. 1, M, E, L, R, R, L, D, C and Fmoc-b-Ala-OH were sequentially attached to resins. Fmoc-protecting group was removed by incubating with the deprotection solution twice for 10 min. 100 mmole of FITC dissolved in DMF were mixed with 200 mmole of DIEA, added to the resin and kept to react for 1 hr, followed by washing. The prepared peptidyl resins were washed three times sequentially with DMF, MC and methanol, dried under the flow of nitrogen gas, completely dried by vacuum-drying under $P_2O_5$ and then reacted with 30 ml of the leaving solution [containing 81.5% TFA, 5% distilled water, 5% thioanisole, 5% phenol, 2.5% EDT and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 0.78 g of unpurified FITC-b-Ala-CDLRRLEMYC (yield 52.6%). Thereafter, the cyclization was carried out using Cys residues at the C-terminal and 1 amino acid apart from the N-terminal of the peptide. 100 mg of the peptide of FITC-b-Ala-CDLRRLEMYC were dissolved in 1 L of 10% DMSO/deprotection distilled water. After fixing pH to 8.0, the peptide solution was agitated for 8 hr under air to induce oxidation. By preparative chromatography, 45 mg of cyclized FITC-b-Ala-Cys-Asp-Leu-Arg-Arg-Leu-Glu-Met-Tyr-Cys-OH (2,11 cyclized).

Experimental Example 1

Influence of Peptides on Growth of HaCat Keratinocytes and NIH3T3 Fibroblasts

In order to evaluate five peptides prepared in Preparation Examples 1-2 whether they have similar activities of insulin like growth factor-1, SRB (Sulforhodamine B) colorimetric assay was carried out using HaCaT kerationcytes and NIH3T3 fibroblasts according to Rizzino et al method (Rizzino, et al. *Cancer Res.*, 48:4266 (1988)).

Figure 9A:
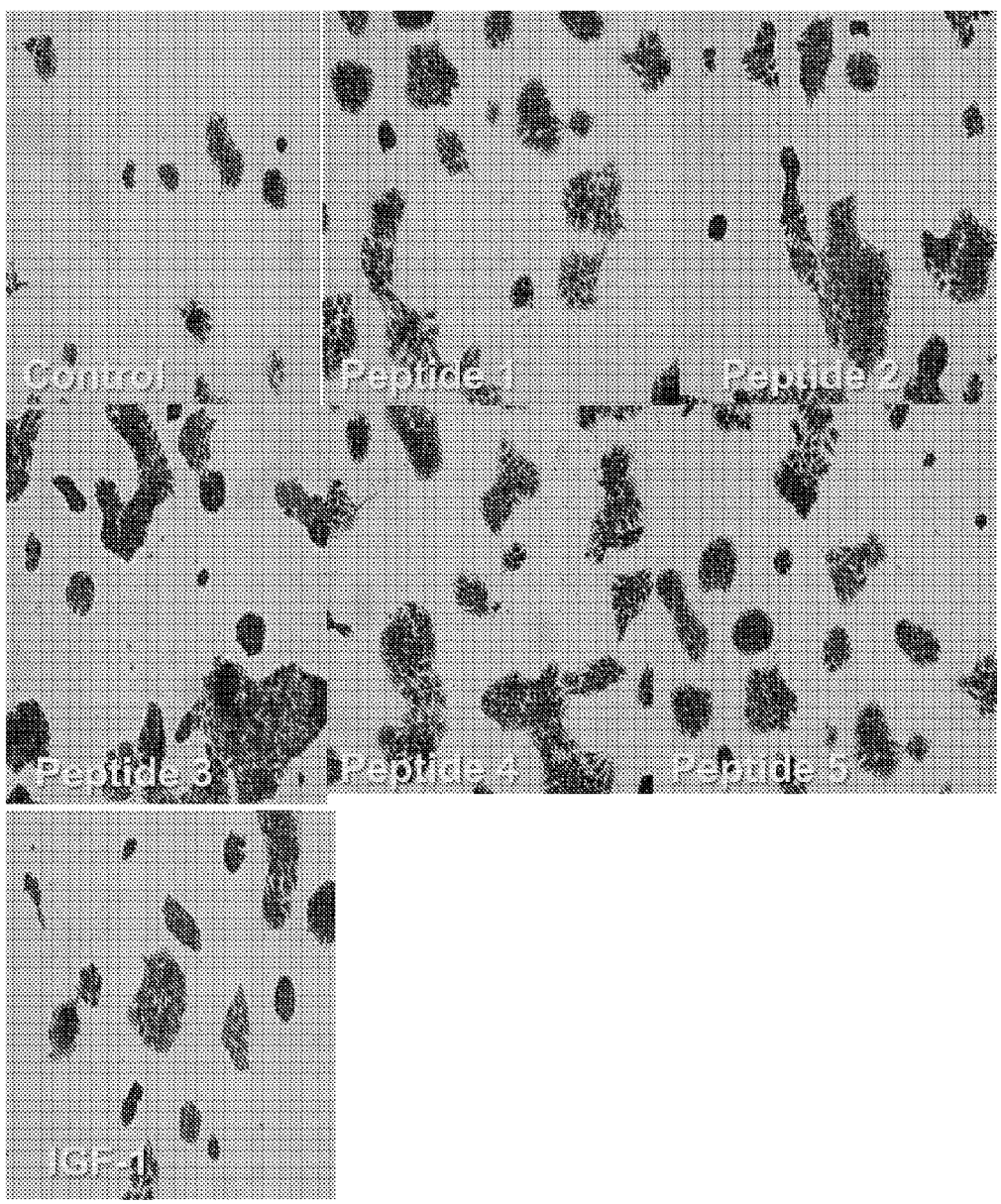
FIG. 9a represents microscopic images demonstrating influence of peptides of this invention on growth of keratinocytes. Peptides 1-5 denote peptides of SEQ ID NOs:1-5, respectively.
Figure 9B:
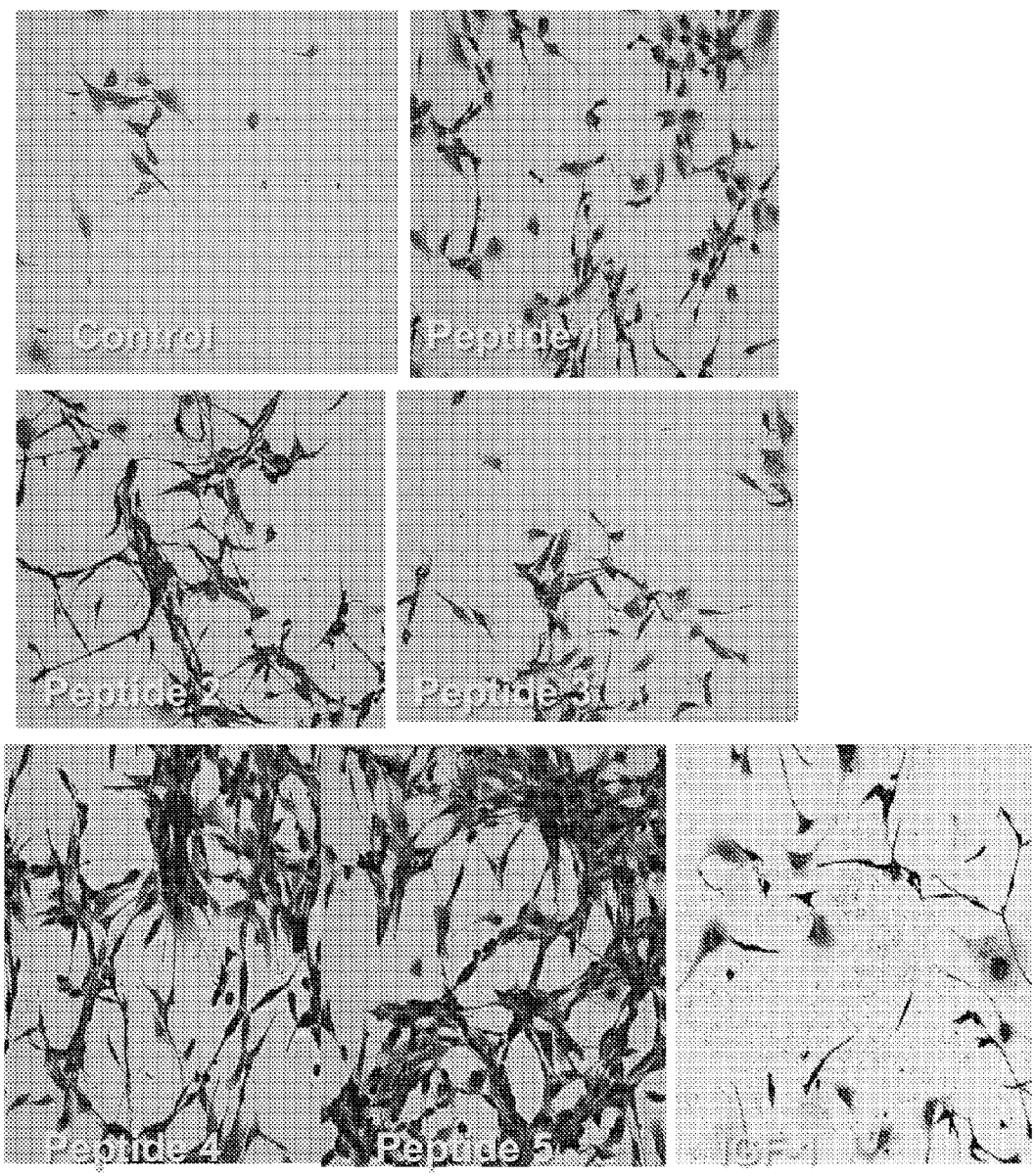
FIG. 9b represents microscopic images demonstrating influence of peptides of this invention on growth of fibroblasts. Peptides 1-5 denote peptides of SEQ ID NOs:1-5, respectively.

HaCaT ketatinocytes (The Korean Cell Line Bank) and NIH3T3 fibroblasts (The Korean Cell Line Bank) were cultured in 250 ml-flasks containing EMEM (Eagle's minimal essential media, Gibco, U.S.A.) supplemented with 100% FBS (fetal bovine serum). Cells cultured were treated with 0.25% trypsin solution to detach cells from the bottom of culture flasks and centrifuged to collect cell pellets. Cells were resuspended in EMEM not containing FBS, its aliquot ($4 \times 10^3$ cells) was added to each well of 96-well plates and cultured under 7% $CO_2$ for 24 hr at 37° C. After 24-hr culture, the medium was changed with a fresh medium not containing serum and cells were incubated with human insulin like growth factor-1 (NIBSC, UK) or five peptides synthesized (10 ng/ml or 1,000 ng/ml) dissolved in 10% DMSO for 72 hr under the same conditions as described above. After removing supernatants, cells were washed once using PBS (phosphate buffered saline) and incubated with SRB solution (Sigma-Aldrich). Cells were washed with PBS and observed under a microscope to find cell viability. In addition, absorbance at 590 nm was measured to analyze cell proliferation. FIG. 8 represents the analysis data for growth of keratinocytes. After 72 hr-treatment with peptides, the growth pattern of keratinocytes was observed under microscope (FIG. 9a: keratinocytes, FIG. 9b: fibroblasts).

As shown in FIG. 8, the five peptides of this invention dramatically promote growth of keratinocytes, which is much better effects than natural-occurring IGF-1. In addition, as shown in FIGS. 9a and 9b, it was observed that the peptides of this invention facilitate growth of fibroblasts as well as keratinocytes.

Furthermore, keratinocytes was treated with the peptides of this invention and the levels of procollagen, laminin and fibronectin, indicators to show the improvement in skin wrinkle, were examined. Kerationcytes cultured for 48 hr were incubated with 5 μmole of peptides of the present invention for 72 hr. The quantification was conducted using Procollagen ELISA kit (Takara, Japan), Laminin ELISA kit (CHEMICON, USA) and Fibronectin kit (Takara, Japan).

Figure 11A:
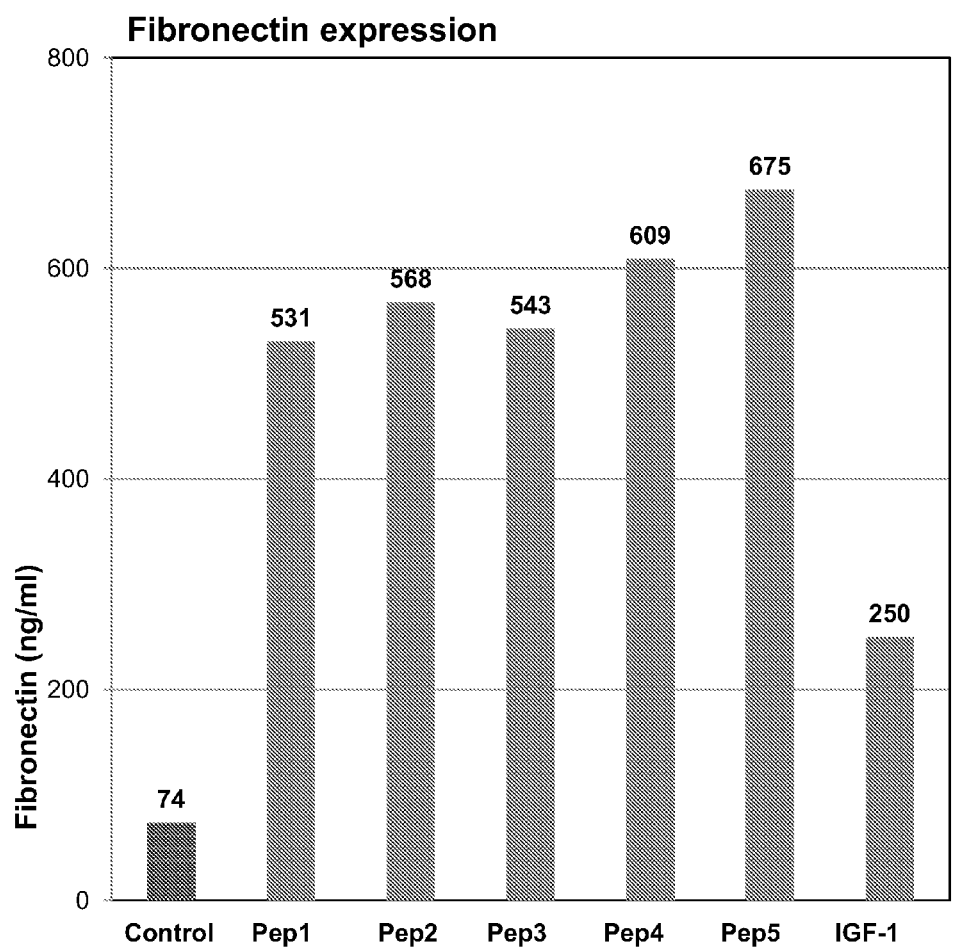
FIGS. 11a and 11b represent analysis results on elevated laminin (FIG. 11a) and fibronectin (FIG. 11b) levels in cell culture incubated with peptides of this invention. Pep 1-5 denote peptides of SEQ ID NOs:1-5, respectively.
Figure 11B:
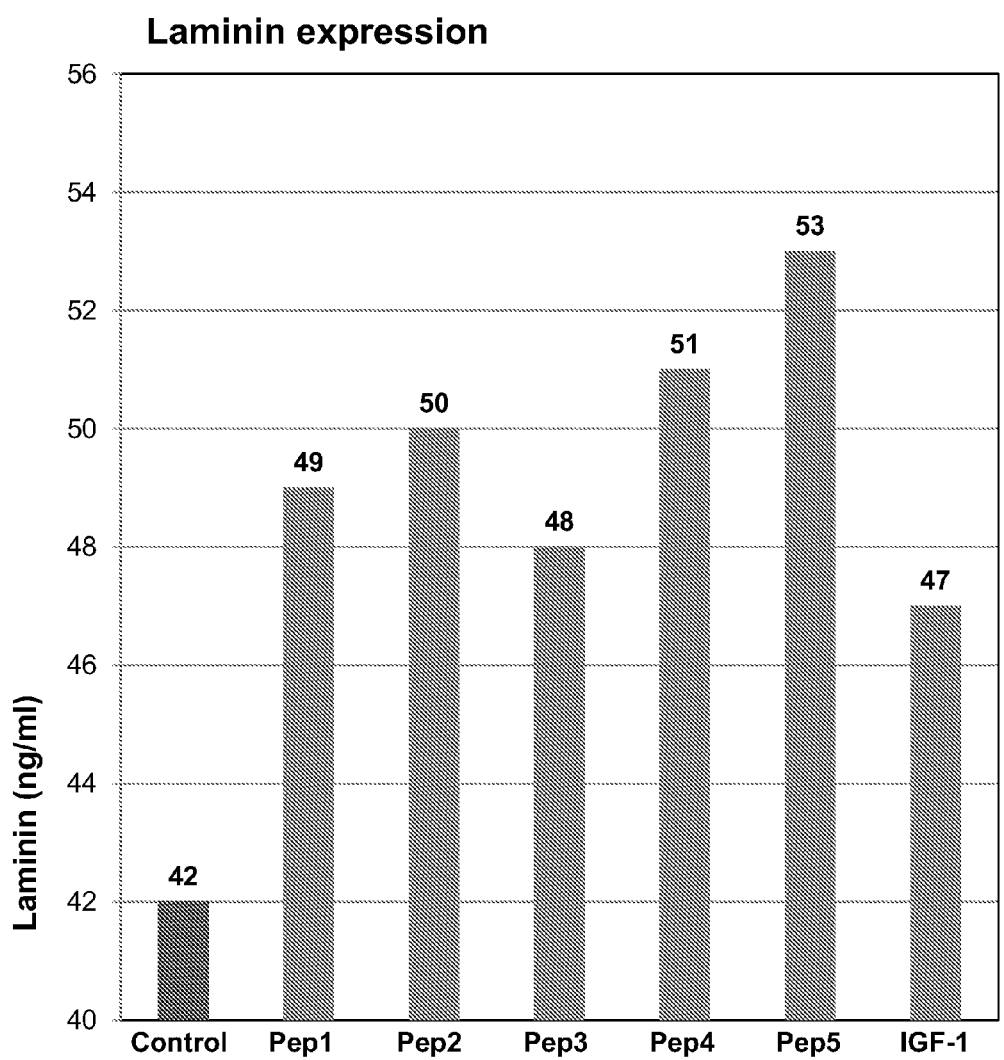

As represented in FIGS. 10 and 11a-11b, the peptides of the present invention were revealed to elevate the level of procollagen, laminin and fibronectin in cells.

Taken together, these results demonstrate that the peptides of the present invention exhibit significant effects to improvement in skin conditions.

Experimental Example 2

Measurement of Binding of Fluorescence-Labeled Peptides to Receptors on Fibroblasts 3T3 fibroblasts were cultured in 250 ml-flasks containing EMEM (Eagle's minimal essential media, Gibco, U.S.A.) supplemented with 100% FBS (fetal bovine serum). After 48-hr culture, the supernatant of the medium was discarded and the remainder was washed once with PBS (phosphate buffered saline). FITC-b-Ala-CDLRRLEMYC prepared in Preparation Example 4 was dissolved in DMSO and PBS to a concentration of 1 mg/ml and incubated for 1 hr with cells cultured. After removing medium, cells were completely washed and their surface was observed under fluorescence and optical microscopes.

Figure 12:
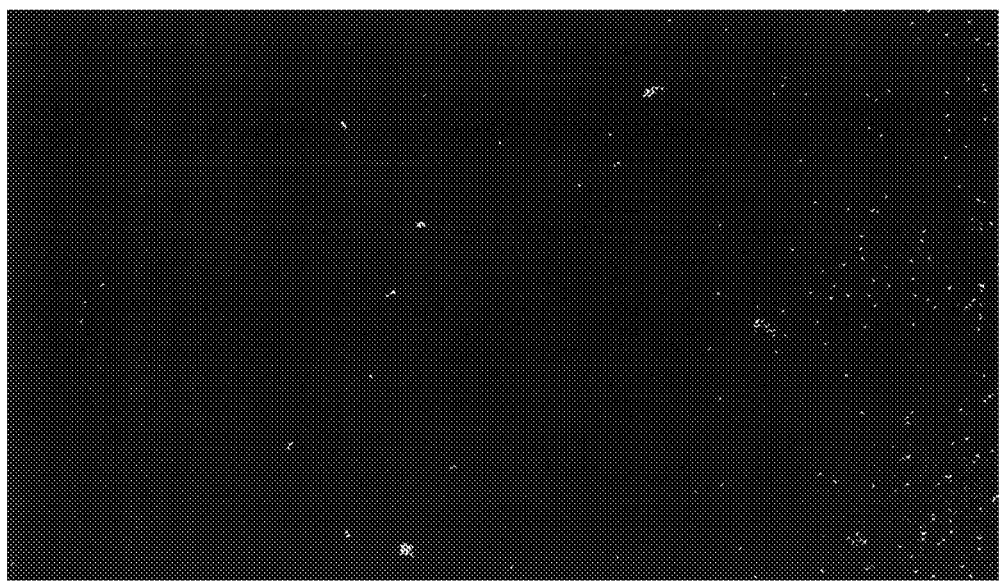
FIG. 12 represents images demonstrating that the peptide of the present invention binds to receptors on cell.

FIG. 12 represents the results of measurement of binding of the FITC-labeled peptide to receptors on cell. The peptide of the present invention binds to receptors on surface of fibroblasts.

Formulation Example 1

Preparation of Nano Peptides 50 mg of the peptide synthesized in Preparation Example 3 was dissolved in 500 ml of distilled water. The peptide solution was mixed with 5 g lecithin, 0.3 ml sodium oleate, 50 ml ethanol and a small amount of oils and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics.

Formulation Example 2

Preparation of Skin Softener Using Nano Peptides

A skin softener containing peptide nanosomes prepared in Formulation Example 1 was formulated according to the following composition:

TABLE 2

| Ingredients | Content (wt %) |
| --- | --- |
| Peptide nanosomes | 10 |
| 1,3-butylene glycol | 6.0 |
| Glycerine | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 3

Preparation of Nutrient Cream Using Nano Peptides

A nutrient cream containing peptide nanosomes prepared in Formulation Example 1 was formulated according to the following composition:

TABLE 3

| Ingredients | Content (wt %) |
| --- | --- |
| Peptide nanosomes | 20 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 4

Preparation of Essence Using Nano Peptides

An essence containing peptide nanosomes prepared in Formulation Example 1 was formulated according to the following composition:

TABLE 4

| Ingredients | Content (wt %) |
| --- | --- |
| Peptide nanosomes | 20 |
| Glycerine | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |

TABLE 4-continued

| Ingredients | Content (wt %) |
|---|---|
| Octyldodeceth-16 | 0.4 |
| Ethanol | 6.0 |
| Perfume, preservative, pigments | Proper amount |
| Distilled water | Residual amout |
| Total | 100 |

Formulation Example 5

Preparation of Mouthwash

A mouthwash containing peptides prepared was formulated according to the following composition:

TABLE 5

| Ingredients | Content (wt %) |
|---|---|
| IGF-1 mimicking peptide | 0.005 |
| Ethanol | 15 |
| Glycerine | 10 |
| Polyoxyethylene hydrogenated castor oil | 2 |
| Saccharine | 0.15 |
| Sodium benzoate | 0.05 |
| Perfume | Proper amount |
| Sodium dihydrogen phosphate | 0.1 |
| Coloring agent | Proper amount |
| Distilled water | 72.7 |

Formulation Example 6

Preparation of Toothpaste

Toothpaste containing peptides prepared was formulated according to the following composition:

TABLE 6

| Ingredients | Contents (wt %) |
|---|---|
| IGF-1 mimicking peptide | 0.005 |
| Dicalcium phosphate | 45 |
| Silica | 2 |
| Glycerine | 15 |
| Sodium carboxymethyl cellulose | 1 |
| Carageenan | 0.3 |
| Sodium laurylsulfate | 1.5 |
| Saccharine-Na | 0.1 |
| Perfume | 적량 |
| Sodium paraoxybenzoate | 0.01 |
| Distilled water | 35.09 |

Experimental Example 3

Analysis of Effects of Peptides on Skin Thickness in BalbC Mice

For evaluating applicability to cosmetics and in vivo efficacies of the peptides of this invention, the nutrient cream formulated in Formulation Example 3 was applied onto mouse skin.

6-old-week Balb C male mice (Central Lab. Animal, Inc., Korea) were subjected to one-week stabilization and hairs of their back were partially removed using thioglycolic acid-containing cream. Mice were divided into two groups; one group of which was topically administered with the cream comprising peptide-containing nanosomes and the other group of which was topically administered with cream not containing nanosomes. The application of creams was performed every morning (A.M. 8:30) and evening (P.M. 6:30) for 5 days in the dose of 100 mg. After the application, mice were sacrificed by cervical dislocation and their skin tissues were paraffinized. Paraffinized tissues were sectioned using a microtomb in a thickness of 8 μm and were stained with hematoxyline/eosin, followed by observation under an optical microscope.

Figure 13:
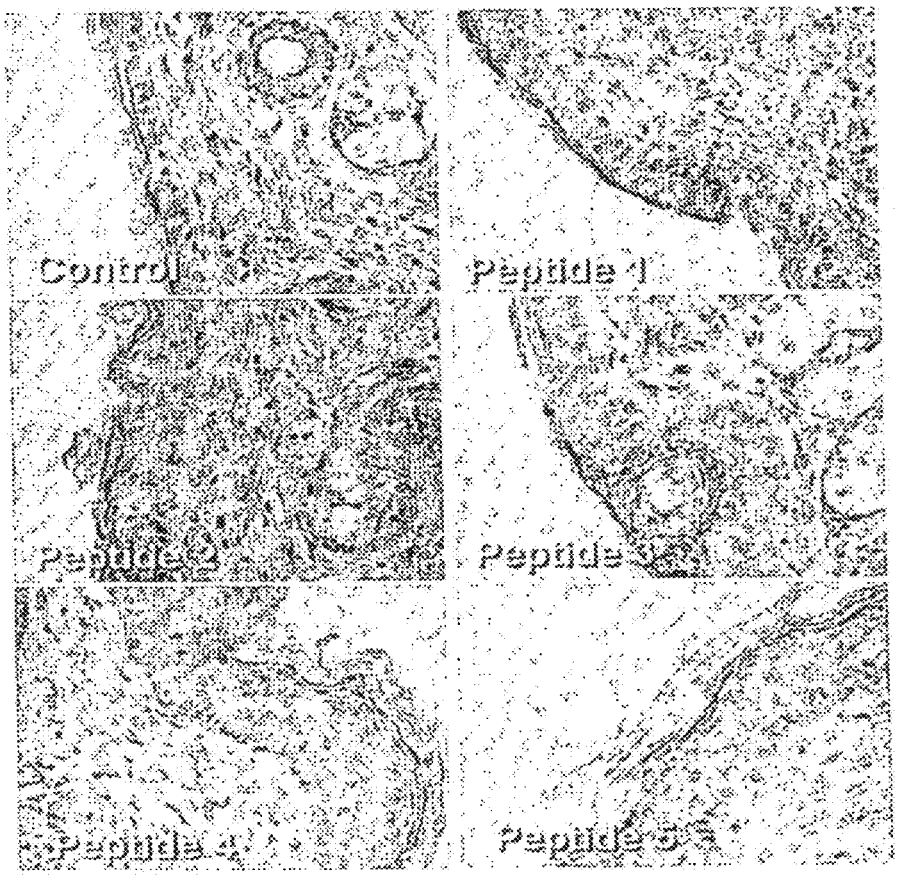
FIG. 13 is a microscope image to show the change in skin thickness of Balb C mice administered with cosmetics containing the peptide of the present invention. Peptides 1-5 denote peptides of SEQ ID NOs:1-5, respectively.
Figure 14:
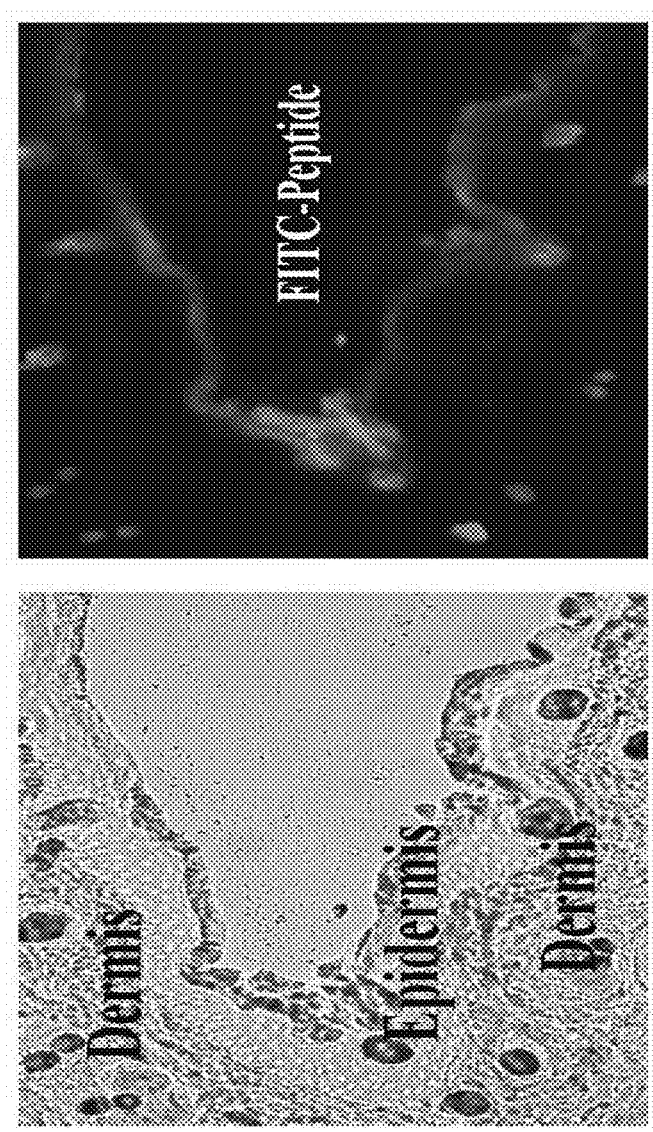
FIG. 14 is a microscope image to show the skin penetration of the fluorescent peptide of the present invention.

As represented in FIG. 13, the nanosome cosmetics comprising the peptide of this invention permitted to promote the formation and growth of keratinocyte layer and epidermal layer. In addition, it was found that the FITC-labeled peptide (SEQ ID NO:3) of this invention was uniformly localized in cells.

Accordingly, it could be recognized that the peptides of this invention accelerate the growth of keratinocytes and epidermal layer, thereby improving skin conditions.

As discussed hereinabove, the IGF-1 mimicking peptides of this invention have identical functions or actions to natural-occurring IGF-1 and much better stability and skin permeation than natural-occurring IGF-1. In these connections, the composition comprising the peptides of this invention can exhibit excellent efficacies on the treatment, prevention and improvement of diseases or conditions demanding IGF-1 activities. In addition, the peptides of this invention can be advantageously applied to pharmaceutical compositions, quasi-drugs and cosmetics.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for improving a skin condition or treating a periodontal disease, which comprises administering to a subject in need thereof a composition comprising an effective amount of a peptide consisting of the amino acid sequence of SEQ ID NO:4.

2. The method according to claim 1, wherein the composition comprises a pharmaceutically effective amount of said peptide and a pharmaceutically acceptable carrier.

3. The method according to claim 1, wherein the composition comprises a cosmetically effective amount of said peptide and a cosmetically acceptable carrier.

4. The method according to claim 1, wherein the improvement in the skin condition is the improvement in wrinkle or skin elasticity, the prevention of skin aging, the prevention of hair loss, the promotion of hair growth, or the improvement in skin moisture.

5. The method according to claim 1, wherein the composition is toothpaste for mouth cleaning or mouth caring.

* * * * *